United States Patent [19]

Djorup

[11] Patent Number: 4,793,181
[45] Date of Patent: Dec. 27, 1988

[54] CONSTANT TEMPERATURE SORPTION HYGROMETER

[76] Inventor: Robert S. Djorup, 20 Lovewell Rd., Wellesley, Mass. 02181

[21] Appl. No.: 57,050

[22] Filed: Jun. 2, 1987

[51] Int. Cl.$^4$ ............................................. G01W 1/00
[52] U.S. Cl. ........................................ 73/336.5; 73/29
[58] Field of Search ................................ 73/336.5, 29

[56] References Cited

U.S. PATENT DOCUMENTS

| | | | |
|---|---|---|---|
| 1,855,774 | 4/1932 | Schneider . | |
| 2,237,006 | 4/1941 | Koller | 201/63 |
| 2,707,880 | 5/1955 | Wannamaker, Jr. | 73/336.5 |
| 3,075,385 | 1/1963 | Stover | 73/335 |
| 3,164,004 | 1/1965 | King | 73/23 |
| 3,253,219 | 5/1966 | Littler | 324/71 |
| 3,350,941 | 11/1967 | Misevich et al. | 73/336.5 |
| 3,523,244 | 8/1970 | Goodman et al. | 324/61 |
| 3,582,728 | 6/1971 | Thoma | 317/246 |
| 3,802,268 | 4/1974 | Thoma | 73/336.5 |
| 4,143,177 | 3/1979 | Kovac et al. | 427/79 |
| 4,164,868 | 8/1979 | Suntola | 73/336.5 |
| 4,379,406 | 4/1983 | Bennewitz et al. | 73/336.5 |
| 4,419,888 | 12/1983 | Kitamura et al. | 73/336.5 |
| 4,562,725 | 1/1986 | Oka et al. | 73/29 |

OTHER PUBLICATIONS

Wexler, A., "Electric Hygrometers", United States Department of Commerce National Bureau of Standards Circular 586, Sep. 3, 1957.
King, W., Jr., "Using Quartz Crystals as Sorption Detectors... Part 1", Research/Development, Apr., 1969 pp. 28–33.
Perry, A. E., "Constant Temperature Hot-Wire Anemometers for the Measurement of Velocity Fluctuations", Hot-Wire Anemometry, 1982, pp. 59–64.
Asch, G., Les Capteurs En Instrumentation Industrielle, Chapter 17, pp. 705–732, published by Dunod (Bordas) Paris, 1983, ISBN 2-04-015635-6.
Krigman, A., "Moisture and Humidity 1985: An Emphasis on Sensor Development", Intech, Mar. 1985, p. 9.

Primary Examiner—Stewart J. Levy
Assistant Examiner—Joseph W. Roskos

[57] ABSTRACT

A constant temperature sorption hygrometer comprising a differential pair of substrate-supported heated metal film sensing elements, one coated with a hygroscopic layer of microporous aluminum oxide and the other coated with a non-hygroscopic protective coating or uncoated, both operated by feedback controlled constant temperature bridge circuits; together with alternate forms of hygrometer transducer apparatus employing differential sorption detection of water vapor.

22 Claims, 2 Drawing Sheets

CONSTANT TEMPERATURE SORPTION HYGROMETER

BACKGROUND OF THE INVENTION

This invention relates generally to improved hygrometer apparatus for measuring atmospheric water vapor content. The invention is particularly concerned with differential constant temperature sorption hygrometer transducer apparatus and constant temperature operation for the apparatus that have sensitive and stable performance, and which may be fabricated simply and economically. The invention also describes techniques for implementing its teachings in alternative transducer structures for application in a contained space or in free space.

The art of electric hygrometry is a mature and well developed art. Many, if not most, materials sorb and desorb water vapor as the ambient relative humidity increases or decreases. Associated with this sorption, there is usually a corresponding change in one or more properties of the material. To be useful in a hygrometer, the material used should have a reversible and reproducible humidity-property characteristic. Properties of air have been used to determine humidity and, in particular, a differential heat loss measurement of thermal conductivity as an indication of humidity is taught by U.S. Pat. No. 1,855,774. The invention disclosed apparatus that may be said to be the electrical counterpart to a wet bulb-dry bulb thermometer pair. A differential measurement is made by a heated resistor pair, one resistor in a reference or control volume, and the second exposed to the surrounding ambient environment.

The use of metal oxides in moisture sensing, and aluminum oxide in particular, is taught by U.S. Pat. No. 2,237,006 which describes a capacitance type moisture sensor using aluminum oxide as a hygroscopic layer between capacitor plates. U.S. Pat. No. 3,075,385 further develops the approach by using aluminum oxide as a dielectric in a capacitance hygrometer for radiosondes. U.S. Pat. Nos. 3,523,244 and 4,143,177 also describe capacitance hygrometers which use aluminum oxide as a moisture sensitive element between capacitor plates and the latter patent teaches us the use of aluminum oxide and silicon dioxide as moisture responsive elements in semiconductor device constructions where a closed volume measurement of water vapor content is desired.

Prior art hygrometer sensors are generally operated at ambient temperature and can easily become loaded with moisture which limits their response. Wet air-dry air reference system are cumbersome and are difficult to use in field operations. Aluminum oxide humidity sensors often demonstrate poor calibration stability owing to ambient temperature operation. The reaction of aluminum oxide with water, as in the aluminum oxide-hydroxide reaction rate, manifests itself as calibration instability, often confused with hysteresis. Many of these same deficiencies are exhibited by capacitive hygrometer transducers which use hygroscopic film materials as a dielectric. In particular, if such transducers become wet or saturated, an extremely long time must pass until they dry off and again become responsive to atmospheric moisture change.

SUMMARY OF THE INVENTION

The present invention overcomes many of the problems encountered by prior hygrometer sensors and provides a significant improvement in hygrometer transducer performance and speed of response by employing controlled constant temperature operation of the active transducer element. In doing so, it is as if the entire surrounding environment around the transducer was at the controlled temperature. Apparatus is provided to desorb or dry off the hygrometer transducer periodically or on demand. Improved differential constant temperature sorption hygrometer transducer means where the entire transducer mechanism is exposed to the ambient environment without a need for a controlled or confined reference is disclosed.

The constant temperature hygrometer transducer according to the instant invention includes two identical sensing elements save for the outermost coating where, on one element, the coating is hygroscopic and, on the second element, the coating or surface is non-hygroscopic. The transducer is operated and excited by feedback controlled electrical circuitry to operate the resistive conductor transducer sensing element pair at constant temperature (constant resistance) and differential electrical circuitry to sense or read out the amount of sorbed water vapor. In a preferred embodiment the active hygroscopic or adsorptive coating is aluminum oxide which is anodized from aluminum metal deposited upon a platinum resistive conductor and the opposite or second element of the pair is either uncoated or is coated with a non-hygroscopic protective overglaze when the transducer is to be exposed to the ambient environment. With the resistive conductor sensing element pair connected into a feedback controlled Wheatstone bridge, used to control operation of the sensing elements at a preset constant temperature above the surrounding ambient temperature, the combination becomes a constant temperature differential sorption hygrometer.

Embodiments are disclosed wherein the transducer elements are in the form of flat plates. A further embodiment discloses that a single plate may contain and support both sensing elements, the uncoated element as well as the hygroscopically coated element. In yet a further embodiment, deposition of a transducer element pair on an arbitrary common or separated substrate geometry is disclosed; and for each embodiment the element may, depending upon its geometry, be either contained and operated in a closed space or in free space.

The instant invention overcomes many of the problems associated with prior art hygrometer sensors respecting moisture loading and instability since the present invention discloses operating the hygrometer sensors under optimum constant temperature conditions and also provides for desorbing the hygrometer sensors on command. Maximum advantage may be taken of the sensitivity of microporous metal oxides and other adsorptive materials by applying them to a single element of an exposed differential pair of elements without the need to establish a controlled or isolated environment for one element to be used as a fixed reference.

DESCRIPTION OF THE PREFERRED EMBODIMENT

Figure 1:
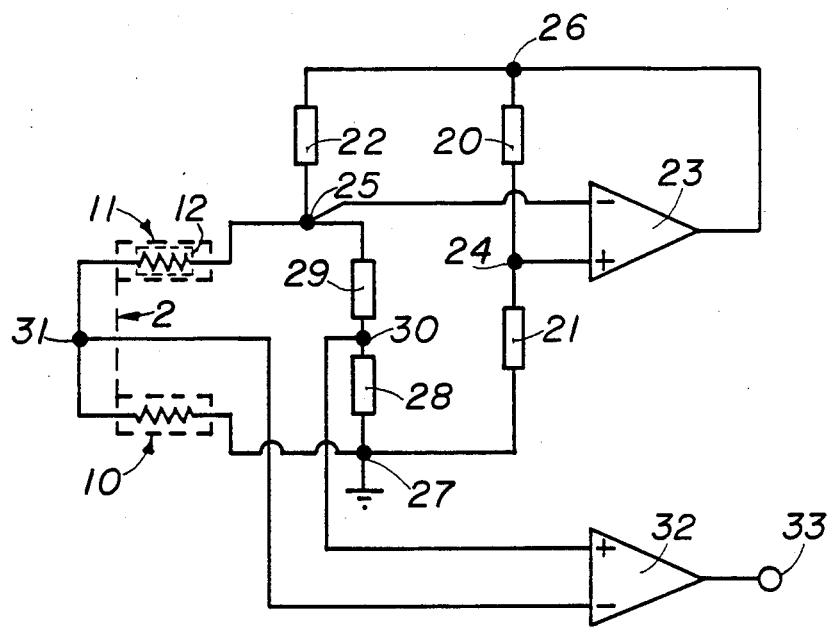
FIG. 1 is a simplified electrical schematic of a preferred embodiment of a constant temperature sorption hygrometer made in accordance with the principles of the present invention.

Referring now to the drawing, and in particular to FIG. 1, the numerals 10 and 11 generally designate a sensing element pair that collectively form a sorption hygrometer transducer 2 constructed in accordance with the principles of the present invention. An important feature of the invention is that sorption hygrometer transducer 2 element pair 10 and 11 are operated at an automatically controlled constant temperature whereby uniform sensitivity to water vapor is repeatably established and the sensing element itself may easily be cleared of moisture, or desorbed, upon command without compromising speed of response. A preferred embodiment of the invention is shown in FIG. 1 wherein a differentially operated sensing element pair, 10 and 11, are controlled and operated as a constant temperature sorption hygrometer. Transducer mechanism 2 employs two near-identical refractory substrate-supported platinum film resistors or sensing elements 10 and 11 wherein element 10 is coated with a smooth protective layer of glass-like material and element 11 is coated with a microporous aluminum oxide layer 12 (FIG. 2) capable of adsorption of water vapor molecules. FIG. 1 illustrates a bridge within a bridge; more specifically, a transducer bridge within a feedback controlled constant temperature (constant resistance) bridge wherein the feedback controlled bridge is used to set and maintain an elevated operating temperature of the transducer sensing element pair and the transducer bridge is used to read out the amount of water vapor that is sorbed by one of the sensing elements of the heated transducer sensing element pair. The depicted differential readout means enables us to ignore common mode phenomena such as ambient environmental changes, air flow variations, temperature changes and the like while non-common mode differential input phenomena cause a significant signal output. The presence of a water vapor sensitive outer layer of microporous aluminum oxide on one of the two otherwise identical heated resistors forces a differential response of the transducer element pair as water vapor content of the surrounding atmosphere increases.

Generally, solid surfaces, and metal oxides in particular, tend to adsorb gases to lower their surface energy. Heat is liberated from an area of the surface when molecules of gas are adsorbed and the phenomenon has been referred to as "chemisorption". The thermal mass of an adsorptive material coated sensing element increases with an increase in adsorbed gas and the choice of adsorbant determines which gas is adsorbed. Heated sensing element equilibrium is achieved by heat transfer to the surrounding atmosphere and by heat balance with the surrounding micro atmosphere. Heat transfer is, for the heated sensing element, by radiation, convection and conduction where, in this case, convective heat transfer is the predominant cooling mechanism employed to establish thermal equilibrium. Natural convection is induced by sensing element self heating and forced convection by surrounding ambient air motion.

It is the aluminum oxide coating 12 that is responsive to changes in ambient humidity or atmospheric water vapor content. Aluminum oxide sorption hygrometers are notable for their intrinsic fast response owing to thinness of the aluminum oxide coating coupled with high adsorption efficiency. Some $7.7 \times 10^{10}$ pores per square centimeter with a diameter of 100 to 300 Angstroms are obtained with an effective adsorption surface area of up to 0.2 square meters per square centimeter of aluminum oxide coating 12. Humidity measurement is effected by determining the amount of differential heat transfer to the surrounding atmosphere by a coated heated sensing element that is compared with an uncoated heated sensing element. Aluminum oxide sorption hygrometers respond to the vapor pressure of water over a very wide range of vapor pressures. As a rule, the amount of sorption is proportional to the water vapor partial pressure and inversely proportional to the absolute temperature. The strong affinity of water for aluminum oxide makes these devices highly selective towards water. They do not respond to most other common gases nor to numerous organic gases and liquids. A thick aluminum oxide layer, upwards of 1 um, shows predominantly relative humidity characteristics while with a thin aluminum oxide layer below 0.3 um an absolute humidity characteristic predominates.

Transducer 2 elements 10 and 11 are identical in all respects, save for the outermost material layer. The deposited film resistor coating on each sensing element 10 and 11 is a high temperature coefficient of resistance metal such as platinum so that the resistor itself can be used as a heating element and simultaneously detect its own self-resistance when operated by a feedback controlled bridge circuit.

Transducer 2 element pair 10 and 11 are shown connected as two arms of a four arm Wheatstone bridge that is completed by resistors 28 and 29. Resistors 28 and 29 are used to balance the bridge when the hygrometer transducer 2 is dry or desorbed. This can be done at temperatures above that of the boiling point of water which assures an absence of water vapor. Excitation for the transducer bridge is provided at point 25 and point 27 is connected to ground. Bridge balance between points 30 and 31 is detected and amplified by a differential amplifier 32, thereby providing a signal 33 which is a measure of the degree of balance or imbalance of the transducer bridge. Amplifier 32 may typically be a high gain integrated circuit operational amplifier such as an N.S.C. type LM-108, or equivalent, which is connected as a differential amplifier. Signal output 33 shows imbalance by swinging to either positive or negative polarity when one or the other of the heated sensing element pair 10 or 11 loses heat to the surrounding atmosphere. The illustrated connection for amplifier 32 will produce a positive polarity output 33 when sorption of water vapor by sensing element 11 causes a greater heat loss than that lost by element 10. Since the total series resistance of elements 10 and 11 is held constant during normal operation, any increase in heat transfer away from either sensing element will cause its resistance to decrease while the other element will increase in resistance. The transducer bridge, formed by the resistors 28 and 29 together with sensing elements 10 and 11 can be considered electrically to be as a single resistor that in turn becomes one arm of a second Wheatstone bridge, or heating bridge, which is formed by a power resistor 22 in series with the transducer bridge, and by resistors 20 and 21. The value of resistors 20 and 21 determines the operating point and balance of the heating bridge and either resistor 20 or 21 can be varied at the time of bridge design. Either resistor 20 or 21 may be a potentiometer or switched resistor although prudent engineering practice suggests that one should remain fixed. It is preferred to keep resistor 20 fixed. Heating bridge excitation is provided at connection 26 and is returned to ground at point 27. Bridge balance between points 24 and 25 is detected and amplified by differential amplifier 23, thereby providing a signal at 26 which is a measure of the degree of balance or imbalance of the heating bridge. Amplifier 23 is a differential amplifier with high current output which is fed back in closed loop fashion to the heating bridge at 26 and attention must be paid to proper input phasing in order to assure that negative feedback is used. Typically, amplifier 23 may be an integrated circuit operational amplifier such as the N.S.C. type LM-112 whose output current may be increased by an emitter follower transistor booster amplifier as is commonly done by those who are experienced in the instrumentation art. When the sensing elements 10 and 11 are cold or are non-operating, their resistance is lower than their normal operating value, and in controlling their operating value through the setting of the reference resistance ratio of resistor 20 to resistor 21, the heated resistance values required to automatically self-balance the bridge can be pre-selected, all of which is controlled through means of negative feedback through amplifier 23 to the bridge at 26. The feedback loop operates to automatically adjust the current through the total bridge combination until the resistance of sensing elements 10 and 11 attains that value of resistance which balances the bridge. A small offset voltage must be present at the output of amplifier 23 when the circuit is first turned on, and the elements are at ambient temperature, so that the minute bridge current which flows as a result of the offset voltage is sufficient to develop a small error signal between points 24 and 25, thus permitting the circuit to turn itself on to an operating condition. The aforedescribed mode of operation has been described in the art as a constant temperature method or constant resistance method of thermal transducer operation.

In a typical bridge circuit the resistance of sensing element 10 or 11 may, for example, be 5 ohms at a room temperature of 18° C. The power resistor 22 can be 2 ohms and it has a low temperature coefficient of resistance, and adequate physical size, so that self-heating does not cause appreciable change in its nominal resistance value with varying operating current levels since it must pass the full heating current for series elements 10 and 11. With a nominal temperature coefficient of resistance of 3800 ppm/° C. element 10 or 11 will be at a resistance value of about 5.608 ohms for a temperature of 50° C. Resistors 28 and 29 are in the 20,000 to 50,000 ohm range so as not to needlessly load sensing elements 10 and 11 and their effect on the total resistance of the transducer bridge is negligible. If resistor 20 is 499 ohms, the value of resistor 21 required to set the bridge in balance is 2798.4 ohms for sensing element 10 and 11 self-heating temperature of 50° C., a typical operating temperature for sorption hygrometer transducer 2. The boiling point of water, 100° C., may be reached with a value of 3272.4 ohms for resistor 21. Both sensing elements 10 and 11 may be desorbed or dried off by increasing the value of resistor 21 above 3272.4 ohms and an increase to 3509.5 ohms will raise the temperature of sensing elements 10 and 11 to 125° C.

Normal constant temperature sorption hygrometer operation takes place when the sensing element 10 and 11 operating temperature is maintained above the maximum expected dew point temperature. A preferred operating temperature is just above the expected maximum ambient temperature for the air mass surrounding hygrometer transducer 2 since the controlled bridge circuit will turn itself off when the ambient temperature is higher than the element operating temperature selected by the value of resistor 21. When the ambient temperature drops, the controlled bridge circuit will resume normal operation. Resistor 21 may include a combination of switch selected resistors for local or remote programmed operation of randomly selected or cyclic sorption/desorption operation of hygrometer transducer 2.

Figure 2:
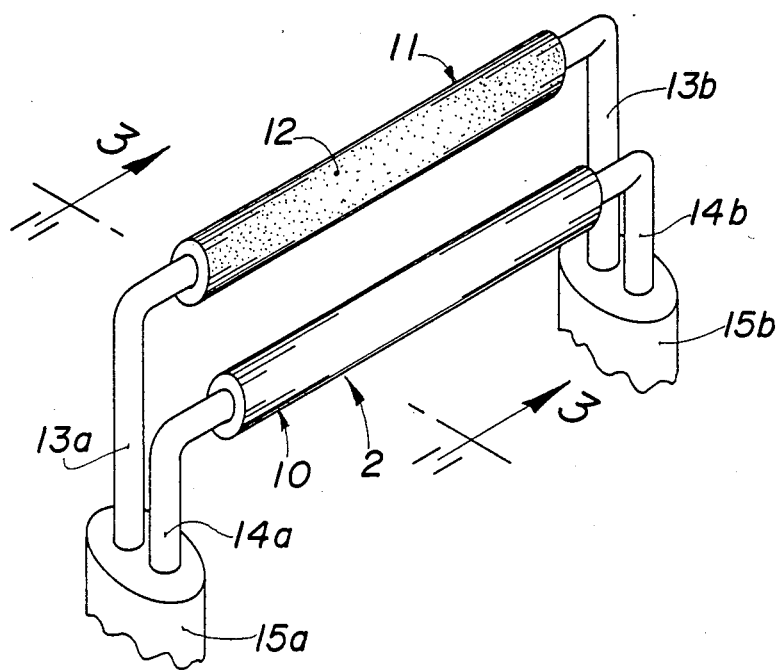
FIG. 2 is a perspective view of a preferred embodiment of a sorption hygrometer transducer made in accordance with the principles of the present invention.

FIG. 2 is a perspective view of a preferred embodiment of a sorption hygrometer transducer 2 constructed in accordance with the principles of the present invention. It is electrically described under FIG. 1. Two near-identical cylindrical sensing elements 10 and 11 are shown, supported by their lead wires 13a, 13b and 14a, 14b, respectively, which are fitted to or supported by an electrically isolating base 15a and 15b. Each sensing element consists of a refractory substrate covered by a resistive platinum metal film and the outside of element 10 is coated with a smooth glazed protective layer of glass-like material and element 11 is coated on the outside with a thin microporous layer of hard hydrated aluminum oxide. In a preferred structure, transducer 2 consists of a separated and similarly oriented pair of heated resistors which are both equally exposed to an open atmospheric environment. Positioning of both elements, 10 and 11, with respect to each other, is such that interference of one with the other is kept to a minimum so that surrounding ambient atmospheric dynamic variations commonly affect both elements in the same manner. If one element sees wind flow, so should the other. Typically, sensing elements 10 and 11 may have a nominal outside diameter of 0.8 mm, with an overall length of 25 mm. Sensing element 10 has a surface area of about 0.63 square centimeters and the application of a smooth protective low surface energy coating minimizes sorption of water vapor. Sensing element 11, on the other hand, has an effective adsorption surface area of about 0.125 square meters owing to the microporous aluminum oxide outer layer. As a result, sensing element 11 has some 2,000 times the water vapor adsorption surface area of sensing element 10, thus facilitating a differential measurement of sorbed water vapor.

A second embodiment of the invention is exemplified by the application of a non zero temperature coefficient resistive conductor to other physical substrate forms such as flat plates wherein the conductor is deposited upon the plate and is coated with a smooth non porous protective layer, and a second identical plate wherein the conductor is coated with a microporous aluminum oxide layer or by other adsorptive material such as a polymer or copolymer film. The plate pair form a sorption hygrometer transducer that is operable as described by FIG. 1 electrical circuit means.

In a further embodiment, the pair of plates can become a single plate-like substrate containing two separate non-zero temperature coefficient resistive conductors, one of which is coated with aluminum oxide or other sorptive material and the other is either uncoated or is smoothly coated with a non-porous protective coating or overglaze. The substrate plate may be fabricated from aluminum oxide or other hard, dense, refractory insulating material or metals that are insulated from the resistive conductor. Differential operation of the element pair is as described by FIG. 1 electrical circuit means.

In yet a further embodiment, the pair of sensing elements can be deposited on any single or paired, arbitrarily shaped, common or separated, substrate geometry, provided that both conductors are the same design and shape and that one conductor is coated with aluminum oxide or other sorptive material and the second conductor is either uncoated or is coated with a non-porous protective coating. In this embodiment both elements are exposed to the same environment. For each of the embodiments the element pair may be contained within a protected volume or, depending upon aerodynamic geometry, the element pair may be exposed in free space.

Figure 3:
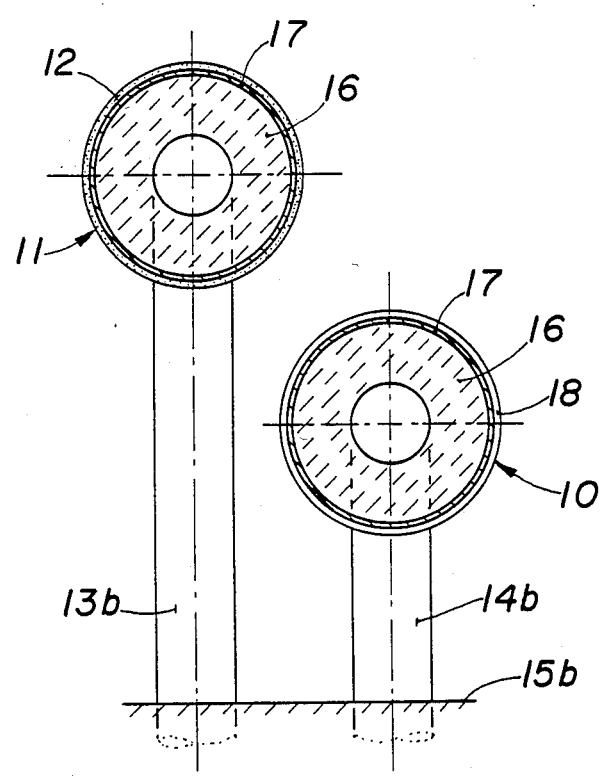
FIG. 3 is an elevational section view of the sorption hygrometer transducer structure illustrated in FIG. 2, taken along the line 3—3 thereof, and looking in the direction of the arrows; and, FIG. 4 is a perspective view of a second embodiment of a sorption hygrometer transducer made in accordance with the principles of the present invention.

FIG. 3 is an elevational section view of the sorption hygrometer transducer structure depicted by FIG. 2, taken along the line 3—3 thereof, and looking in the direction of the arrows. The section is taken through the central portion of a symmetrical structure. Sensing elements 10 and 11 are identically constructed in all respects save for the outermost coating, 18 and 12, respectively. Sensing element 10 consists of an electrically non-conductive, hollow, tubular, dense aluminum oxide refractory fine cylinder substrate body 16 upon which is deposited a platinum film 17 and an overall protective coating 18. The supporting substrate body 16 may be chosen from other suitable materials that are electrically non-conductive, such as quartz, hard glass, mullite porcelain, aluminum silicate and other refractory materials. Substrate materials herein described can be obtained from Degussa Corp., Coors Porcelain Co., and others from their standard inventory. When low operating and fabrication temperatures are to be encountered in film 17 deposition and use, as in certain vacuum coating methods, the substrate 16 can be made of soft glass or even plastic tubing. Typical dimensions for the substrate body 16 are a cylinder diameter of 0.6 mm or 0.8 mm, with a bore diameter of 0.3 or 0.4 mm, and a length of some 20 to 25 mm. The entire sensing element 10 can be scaled larger in size or considerably smaller as the intended application may require.

The connecting lead wire 14b is made of platinum, a material similar to the platinum metal film 17, in order to avoid unwanted thermocouple junction effects, keep electrical noise to a minimum, and thereby to help to attain maximum long term stability. Attachment of lead wire 14b to substrate 16 may be made by use of platinum sponge or platinum paste which is brushed onto the lead wire which is inserted a short distance into the substrate 16 bore and then fired in air in an electric kiln or conveyor furnace. Several coats are applied to the end connection until a neat fillet is formed and care must be taken to make all end connections the same in order to preserve physical and thermodynamic similarity from connection to connection and element to element. Typical platinum paste which may be used is Engelhard Industries #6082 or #6926 which are fired at about 850° C. to 900° C. The lead wire and substrate assembly next receives a resistance film coating 17 of platinum metal typically in the order of 2 to 10 microns thickness with an electrical resistance of several ohms. It can vary in accordance with the particular coating method which is selected. Several different coating methods may be used and these may range from vacuum sputtering or plasma deposition to the simple "paint and fire" technique. The latter technique borrows from the ancient methods used by the artist or pottery and china maker. Useful materials include the noble-metal resinate solutions which may be applied by brushing, dipping, or spraying, then furnace firing, with repeated application of multiple coats until the desired film resistance is achieved. Engelhard Industries #05-X liquid bright platinum is a preferred resinate which may be applied with a small sable brush. Firing temperatures, in air, are in the 800° C. range.

The resistive platinum film coating 17 has a further layer 18 of vitreous enamel, glass overglaze, fused silica, fused quartz, or other protective material which provides abrasion and wear protection for the exposed platinum film 17. It is important that the material which is chosen for protective coating 18 is stable and inert, is non-porous, has a low surface energy, and does not change with time and extended exposure to the intended environment for the transducer 2. An example of an inert vitreous overglaze which is compatible with platinum metal is Engelhard Industries #6624 squeegee overglaze that is fired at 625° C. in air. The protective layer 18 can be applied over the entire outer surface of the sensing element body 10 with attached lead wires, by dipping, brushing or spraying. The protective layer 18 thickness is usually less than 0.025 mm thick and most often is used in the range of 0.006 mm thick after firing. The protective layer 18 is extended to include the area where resistive platinum film 17 overlaps platinum lead wire 14b thereby protecting the electrical connection at the end of sensing element body 10.

Sensing element body 11 is the same as element 10 save for the outermost coating layer 12 which, in the former case, is deposited as aluminum metal and then converted to microporous aluminum oxide. The aluminum metal layer can be applied by using aluminum ink, electro-deposition, or vacuum deposition techniques. The use of aluminum ink is least costly and requires no exotic or complex equipment. Examples of aluminum inks are Engelhard Industries #A-3113 and #A-3484. Aluminum inks are also fired in air and at temperatures in the 550° to 675° C range. Under certain conditions, firing temperatures to 900° C. may be needed to be employed for #A-3113 ink if molecular bonding is intended. The lower temperatures may be used where the aluminum is placed directly over the platinum metal conductor which has a slightly matte surface finish after firing. The higher temperature is indicated if any of the substrate is exposed and is to be covered with aluminum.

After firing, the surface layer 12 of aluminum is oxidized to form a microporous aluminum oxide layer, also shown as 12 in FIG. 3 because of the complete material conversion which is to take place. Typically, the oxide may be formed by an anodizing process in which an alternating current is passed through a heated sulphuric acid solution containing suspended sensing element assembly 11 where electrical connection is made by clips to lead wires 13a and 13b which are not coated by aluminum. The acid solution may include 20% to 70% sulphuric acid by volume and is externally heated, by suitable heating means, to a temperature of about 21° C. to 38° C. An alternating current of 54 to 270 amperes per square meter of anodizing surface passes through the solution while the sensing element is suspended therein. The period of time ranges from 10 to 80 minutes depending on the percentage of acid in solution, solution temperature, current density, and the desired depth of the anodize. It has been reported in prior art patents and in instrumentation texts that satisfactory anodized coatings have been obtained by using a 50% sulphuric acid solution having a specific weight of 1.4 maintained at 90° F. (32.2° C.), with alternating current of 12 amperes per square foot (129 amperes per square meter) of anodizing surface for a period of 25 to 30 minutes. Completeness of the anodize may be determined by measuring the electrical resistance of sensing element 11 which will increase to the resistance value of the platinum resistor 17 when all of the aluminum metal is converted to aluminum oxide.

After anodizing it may be necessary to stabilize the aluminum oxide ($Al_2O_3$) coating in order to avoid change in moisture adsorption qualities as a function of time and exposure. This can be accomplished by boiling the sensing element 11 in distilled water for a period of 30 to 45 minutes after which the surface is scrubbed with a brush to remove the fairly loose layer of aluminum oxide powder which may have formed during boiling water aging. This leaves the hard stable form of hydrated aluminum oxide, the monohydrate or crystalline modification called boehmite ($\gamma$-$Al_2O_3 \cdot H_2O$).

A final aging step that is analogous to solution annealing may be applied to the completely fabricated hygrometer sensing element 11 in order to drive off impurities or hygroscopic materials picked up during manufacture, to stabilize the aluminum oxide "grain" size and reduce the presence of fissures and cracks. This may be accomplished by baking the sensing element at a temperature from 200° C. to 350° C. for a period of time between 30 and 90 minutes. As a precaution, in order to assure a degree of manufacturing symmetry or "sameness", sensing element 10 may also be subjected to the final aging step. In this way, both platinum film resistor elements, 17, of the sensing element pair, will be stress relieved in the same manner.

In referring collectively to FIGS. 1, 2 and 3, adsorptive material coating layer 12 has been described as aluminum oxide and a method of fabrication has been disclosed. Aluminum oxide is advantageous for use in a sorption hygrometer for reasons herein described, not the least of which is its adsorption efficiency and safety. Certain metal oxides, such as beryllium oxide (BeO), have a high surface energy and can effectively be used as an adsorptive coating, however, this material is extremely hazardous to use in its powdered form and if it is to be used, suitable precautions must be taken. Coating 12 may be a metal oxide, from silicon and nickel and others, hydrated or treated to open up its surface to increase effective sorption area. When lowest cost is a necessary factor the use of a dip-applied hygroscopic coating material becomes attractive, although these materials may result in a less sensitive hygrometer. Many dipped coatings are problematic in use when the atmosphere becomes saturated or the coatings become wet, and they also often exhibit instability and hysteresis. Constant temperature hygrometer operation, as herein described by the instant invention, minimizes many of these shortcomings and, in certain applications, a cycle of desorption/sorption just prior to use can further enhance operation of the hygrometer. Typical hygroscopic polymers include hydroxyl ethyl cellulose, carboxyl methyl cellulose and cellulose esters. Examples of hygroscopic copolymers are vinylene carbonate and vinyl acetate among others. These materials may be solvent dissolved and they can be applied by simply dipping sensing element 11 into the liquid material, then air dried or oven dried, followed by hydrolyzation of the coating by dipping the coated sensing element 11 into an acid or alkaline bath for a period of time. The use of such materials and processing methods is taught by U.S. Pat. Nos. 3,350,941; 3,582,728; 3,802,268 and 4,562,725 which describe moisture sensitive polymers and copolymers which may be applied to electric hygrometer transducer resistor sensing elements.

Arnold Wexler's "Electric Hygrometers", published on Sept. 3, 1957, National Bureau of Standards Circular 586, U.S. Government Printing Office, Washington, D.C., further identifies useful sorptive coating including metal oxide films, salt films and polymeric resins which may be applied to transducer sensing element 11 for use as the moisture sensitive coating 12.

Figure 4:
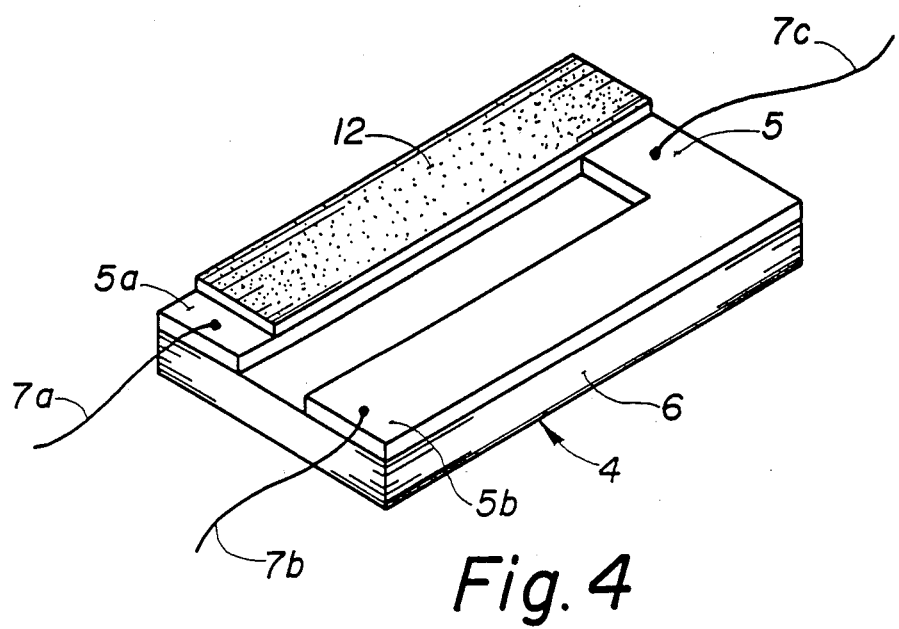

FIG. 4 is a perspective view of an embodiment of a sorption hygrometer transducer 4 constructed in accordance with the principles of the present invention. It is electrically similar to hygrometer transducer 2 and is operatively described under FIG. 1. Functionally, hygrometer transducer 4 comprises a center tapped resistor wherein one half is hygroscopically sensitive and the other half is hygroscopically insensitive. Resistive metal film 5 is deposited on refractory substrate 6 wherein said metal film is divided into two parts, 5a and 5b, one part 5a coated with a sorptive material layer 12 and the other part 5b is uncoated. A preferred coating 12 is microporous aluminum oxide and a preferred metal film 5 is platinum, deposited on dense aluminum oxide substrate 6. Lead wire connections 7a and 7b are made to each end of connector 5 with lead wire 7c attached to the center point. Lead wire connections can be made by using platinum paste as hereabove described by FIG. 3, or they may be welded or soldered to film 5.

Although this specification has described hygroscopically coated add uncoated films in film resistor pairs which are identical, save for the coating, it should be understood that as long as the resistor film temperature coefficient of resistance is identical, the individual film resistor values may differ and be balanced by similarly differing balancing resistors which are part of the hereabove described transducer bridge.

What is claimed is:
1. Hygrometer comprising:
    a pair of temperature coefficient resistive sensing elements, one of the elements including a hygroscopic material and the other element being substantially non-hygroscopic;
    a transducer Wheatstone bridge including the pair of sensing elements as two of the transducer bridge arms;
    a heating Wheatstone bridge including the transducer bridge as one arm of the heating bridge;
    a feedback controlled electrical circuit adapted to maintain the resistance of the transducer bridge constant; and
    circuitry adapted to measure the transducer bridge imbalance, the imbalance being relate to the amount of water adsorbed by the sensing element including the hygroscopic material.
2. The hygrometer of claim 1 wherein the hygroscopic material is aluminum oxide.
3. The hygrometer of claim 1 wherein the hygroscopic material is a hygroscopic polymer.

4. The hygrometer of claim 1 wherein the hygroscopic material is a hygroscopic copolymer.

5. The hygrometer of claim 1 wherein the hygroscopic material is hydroxyl ethyl cellulose.

6. The hygrometer of claim 1 wherein the hygroscopic material is carboxyl methyl cellulose.

7. The hygrometer of claim 1 wherein the hygroscopic material is a cellulose ester.

8. The hygrometer of claim 1 wherein the hygroscopic material is vinylene carbonate.

9. The hygrometer of claim 1 wherein the hygroscopic material is vinyl acetate.

10. The hygrometer of claim 1 wherein tee hygroscopic material is beryllium oxide.

11. The hygrometer of claim 1 wherein the hygroscopic material is a metal oxide.

12. The hygrometer of claim 11 wherein the metal oxide includes silicon.

13. The hygrometer of claim 11 wherein the metal oxide includes nickel.

14. The hygrometer of claim 1 wherein the sensing elements include a cylindrical refractory substrate coated with a conductive material.

15. The hygrometer of claim 14 wherein the conductive material is platinum.

16. The hygrometer of claim 14 wherein the hydroscopic material of one of the elements forms a coating over the conductive material.

17. The hygrometer of claim 16 wherein the hygroscopic coating is aluminum oxide.

18. The hygrometer of claim 14 wherein the substrate is aluminum oxide.

19. The hygrometer of claim 1 wherein the pair elements are both mounted on a single substrate.

20. The hygrometer of claim 19 wherein the substrate is substantially flat.

21. The hygrometer of claim 1 wherein the circuit adapted to measure the transducer bridge imbalance includes an amplifier connected between the two resistive sensing elements and between two other resistors of the transducer bridge.

22. The hygrometer of claim 1 wherein the feedback controlled electrical circuit includes a differential amplifier.

* * * * *

UNITED STATES PATENT AND TRADEMARK OFFICE
CERTIFICATE OF CORRECTION

PATENT NO. : 4,793,181
DATED : December 27, 1988
INVENTOR(S) : Robert S, Djorup

It is certified that error appears in the above-identified patent and that said Letters Patent is hereby corrected as shown below:

Column 1, line 52, "system" should be --systems--.
Column 3, line 65, "micro atmosphere" should be --micro-atmosphere--.
Column 4, line 2, "self heating" should be --self-heating--.
Column 6, line 55, "non zero" should be --non-zero--;
         line 58, "non porous" should be --non-porous--.
Column 10, line 16, "coating" should be --coatings--;
          line 40, "add" should be --and--;
          line 62, "relate" should be --related--.
Column 11, line 16, "tee" should be --the--.
Column 12, line 13, after "pair", insert --of sensing--.

Signed and Sealed this

Sixteenth Day of May, 1989

Attest:

DONALD J. QUIGG

Attesting Officer

Commissioner of Patents and Trademarks